(12) United States Patent
Kogan et al.

(10) Patent No.: US 6,713,604 B1
(45) Date of Patent: Mar. 30, 2004

(54) PROCESS TO INHIBIT BINDING OF THE INTEGRIN $\alpha_4\beta_1$, TO VCAM-1 FIBRONECTIN AND CYCLIC PEPTIDES THEREOF

(75) Inventors: Timothy P. Kogan, Sugar Land, TX (US); Kaijun Ren, Sugar Land, TX (US); Peter Vanderslice, Houston, TX (US); Pamela J. Beck, Houston, TX (US)

(73) Assignee: Texas Biotechnology Corporation, Houston, TX (US)

( * ) Notice: Subject to any disclaimer, the term of this patent is extended or adjusted under 35 U.S.C. 154(b) by 0 days.

(21) Appl. No.: 08/646,558

(22) Filed: May 8, 1996

Related U.S. Application Data

(63) Continuation of application No. 08/268,192, filed on Jun. 29, 1994, now abandoned.

(51) Int. Cl.[7] .............................................. C07K 16/00

(52) U.S. Cl. .............................. 530/317; 514/11; 514/9; 514/2

(58) Field of Search .................... 514/11, 9, 2; 530/317; 930/260, DIG. 535, DIG. 536, DIG. 537

(56) References Cited

U.S. PATENT DOCUMENTS 5,192,746 A  *  3/1993  Lobl et al. ..................... 514/11

FOREIGN PATENT DOCUMENTS

| EP | 0341915 | * 11/1989 |
| EP | 0422938 | * 4/1991 |
| WO | 8905150 | * 6/1989 |

OTHER PUBLICATIONS

Pierschbacher et al, PNAS, vol. 81, pp. 5985–5988, (Oct. 1984).*
Yamada, The Journal of Biological Chemistry, vol. 266(20), pp. 12809–12812, (Jul. 15, 1991).*
Davies et al, Biochemical Society, Transactions, vol. 18, pp. 1326–1328 (1990).*
Ali et al, Peptides, Proceedings of the 11th Am. Pept. Symp., pp. 94–96, (Jul. 9–14, 1989).*
Aumailley et al, FEBS, vol. 291(1), pp. 50–54, 1991.*
The Journal of Cell Biology, *Activation–dependent Recognition by Hematopoietic Cells of the LDV Sequence in the V Region of Fibronectin*; E.A. Wayner and N.L. Kovach, vol. 116, No. 2, 489–497 (Jan. 1992).
Cell, *Phosphatidylinositol 3–Kinase: Structure and Expression of the 110 kd Catalytic Subunit*, Hiles et al., vol. 70, 419–429 (Aug. 7, 1992).
Journal of Cell Science, *VCAM–1 is a CS1 peptide–inhibitable adhesion molecule expressed by lymph node high endothelium*, May et al., vol. 106, 109–119 (1993).

American Journal of Pathology, *Rapid Communication—Alternative Splicing of Human VCAM–1 in Activated Vascular Endothelium*, Cybulski et al., vol. 138, No. 4, 815–820, (Apr. 1991).
The Journal of Biological Chemistry, *Competitive Binding of Vascular Cell Adhesion Molecule–1 and the HepII/IIICS Domain of Fibronectin to the Integrin $\alpha 4\beta 1$*, Makarem et al., vol. 269, No. 6, 4005–4011, (Feb. 1994).
Cell, *VCAM–1 on Activated Endothelium Interacts with the Leukocyte Integrin VLA–4 at a Site Distinct from the VLA–4/Fibronectin Binding Site*, Elices et al., vol. 60, 577–584, (1990).
Cell, *Direct Expression Cloning of Vascular Cell Adhesion Molecule 1, a Cytokine–Induced Endothelial Protein That Binds to Lymphocytes*, Osborn et al., vol. 9, 1203–1211, (1989).
Science, *An Inducible Endothelial Cell Surface Glycoprotein Mediates Melanoma Adhesion*, G. Edgar Rice and Michael P. Bevilacqua, vol. 246, 1303–1306 (Dec. 1989).
The Journal of Biological Chemistry, *Cloning of an Alternate Form of Vascular Cell Adhesion Molecule–1 (VCAM1)*, Hession et al., vol. 266, Issue No. 11, 6682–6685 (1991).
J. Exp. Med., *Lymphocyte Adhesion through Very Late Antigen 4: Evidence for a Novel Binding Site in thew Alternatively Spliced Domain of Vascular Cell Adhesion Molecule 1 and an Additional $\alpha 4$ Integrin Counter–Receptor on Stimulated Endothelium*, Robert H. Vonderheide and Timothy A. Springer, vol. 175, 1433–1442, (Jun. 1992).
J. Exp. Med., *Activated Endothelium Binds Lymphocytes Through a Novel Binding Site in the Alternatively Spliced Domain of Vascular Cell Adhesion Molecule–1*, Laurelee Osborn and Christopher D. Benjamin, vol. 176, 99–107 (Jul. 1992).
The Journal of Biological Chemistry, *VLA–4 Integrin Mediates Lymphocyte Migration on the Inducible Endothelial Cell Ligand VCAM–1 and the Extracellular Matrix Ligand Fibronectin*, Po–Ying Chan and Alejandro Aruffo, vol. 268, No. 33, 24655–24664 (Nov. 24, 1993).

(List continued on next page.)

Primary Examiner—T. D. Wessendorf
(74) Attorney, Agent, or Firm—Wood, Phillips, Katz, Clark & Mortimer

(57) ABSTRACT

The present invention is directed to an isolated and purified cyclic peptide of from 5 to about 13 residues modeled after a portion of the CS1 peptide. A peptide of this invention preferably has the amino acid residue sequence of SEQ ID NO:2–14 or 16–42. The present invention is further directed to a process of selectively inhibiting the binding of $\alpha_4\beta_1$ integrin to a protein such as VCAM-1, fibronectin or invasin. In accordance with that process, a cell that expresses $\alpha_4\beta_1$ integrin is exposed to that protein in the presence of an effective inhibiting amount of such a peptide. The present invention is still further directed to a pharmaceutical composition containing a physiologically acceptable carrier and a cyclic peptide of the invention.

4 Claims, No Drawings

OTHER PUBLICATIONS

The EMBO Journal, *Identification of a novel recognition sequence for the integrin α4β1 in the COOH–terminal heparin–bindin g domain of fibronectin*, A. Paul Mould and Martin J. Humphries, vol. 10, No. 13, 4089–4095 (1991).

J. Clin. Invest., *VLA–4 Integrin Can Mediate CD11/ CD18–independent Transendothelial Migration of Human Monocytes*, H. Eduardo Chuluyan and Andrew C. Issekutz, vol. 92, 2768–2777 (Dec. 1993).

Nature, *Prevention of experimental autoimmun e encephalomyelitis by antibodies against α4β1 integrin*, Yednock et al., vol. 356, 63–66 (Mar. 5, 1992).

Eur J. Immunol, *Monoclonal antibodies to the integrin α–4 subunit inhibit the murine contact hypersensitivity response*, Chisholm et al., vol. 23, 682–688 (1993).

The Journal of Biological Chemistry, *Multiple Activation States of VLA–4*, Akihide Masumoto and Martin E. Hemler, vol. 268, No. 1, 228–234 (Jan. 5, 1993).

1994 Current Drugs Ltd., Abstract of Publication No. WO 9402445, *Non–peptidic surrogates of the LDV sequence and their use in the treatment of inflammation, autoimmune diseases and tumour progression*, Lider et al.

The Journal of Biological Chemistry, *The CS5 Peptide Is a Second Site in the IIICS Region of Fibronectin Recognized by the Integrin $α_4β_1$*, Mould et al., vol. 266, No. 6, 3579–3585 (Feb. 25, 1991).

\* cited by examiner

US 6,713,604 B1

PROCESS TO INHIBIT BINDING OF THE INTEGRIN $\alpha_4\beta_1$, TO VCAM-1 FIBRONECTIN AND CYCLIC PEPTIDES THEREOF This is a continuation, of application Ser. No. 08/268,192, filed Jun. 29, 1994, now abandoned.

FIELD OF THE INVENTION

This invention relates generally to a process of inhibiting the binding of $\alpha_4\beta_1$ integrin to proteins such as VCAM-1 or fibronectin. The invention also relates to synthetic cyclic peptides that inhibit that binding.

BACKGROUND OF THE INVENTION

Vascular cell adhesion molecule-1 (VCAM-1) is a protein that is found on the surface of endothelial cells that line the interior wall of capillaries. VCAM-1 recognizes and binds to the integrin $\alpha_4\beta_1$ (or VLA-4 for very late antigen-4), a beterodimeric protein present on the surface of certain white blood cells. Binding of $\alpha_4\beta_1$ to VCAM-1 allows white blood cells to adhere to the capillary wall in areas where the tissue surrounding the capillary has been infected or damaged.

When a tissue has been invaded by a microorganism or has been damaged, white blood cells, also called leukocytes, play a major role in the inflammatory response. One of the most important aspects of the inflammatory response involves the cell adhesion event. Generally, white blood cells are found circulating through the bloodstream. However, when a tissue is infected or becomes damaged, the white blood cells recognize the invaded or damaged tissue, bind to the wall of the capillary near the affected tissue and diffuse through the capillary into the affected tissue. VCAM-1 helps certain types of white blood cells recognize the affected sites, bind to the capillary wall, and migrate into the affected tissue.

The are are three main types of white blood cells: granulocytes, monocytes and lymphocytes. VCAM-1 binds to $\alpha_4\beta_1$ expressed on the surface of monocytes, lymphocytes and two subclasses of granulocytes-eosinophils and basophils.

Monocytes, after leaving the bloodstream through the wall of a capillary, mature into macrophages that phagocytose and digest invading microorganisms, foreign bodies and senescent cells. Lymphocytes produce antibodies and kill infected cells. Eosinophils and basophils secrete mediators of various inflammatory reactions.

Following infection or damage of tissue surrounding a capillary, the endothelial cells that line the capillary express a series of adhesion molecules, including VCAM-1, that are critical for binding white blood cells that are necessary for fighting infection. Prior to binding to VCAM-1, the white blood cells initially bind to another set of adhesion molecules to slow their flow and allow the cells to "roll" along the activated endothelium. Monocytes, lymphocytes, basophils and eosinophils are then able to firmly bind to VCAM-1 on the endothelial cells via the $\alpha_4\beta_1$ integrin. There is evidence that this interaction is also involved in transmigration of these white blood cells into the damaged tissue.

Although white blood cell migration to the site of injury helps fight infection and destroy foreign material, in many instances this migration can become uncontrolled, with white blood cells flooding to the scene, causing widespread tissue damage. Compounds capable of blocking this process, therefore, would be beneficial as therapeutic agents. Thus, it would be useful to develop inhibitors that would prevent the binding of white blood cells to VCAM-1.

For example, some of the diseases that might be treated by the inhibition of $\alpha_4\beta_1$ binding include, but are not limited to, atherosclerosis, rheumatoid arthritis, asthma, allergy, multiple sclerosis and type I diabetes. In addition to being found on some white blood cells, $\alpha_4\beta_1$ is found on various cancer cells, including leukemia, melanoma, lymphoma and sarcoma cells. It has been suggested that cell adhesion involving $\alpha_4\beta_1$ may be involved in the metastasis of certain cancers. Inhibitors of $\alpha_4\beta_1$ binding may, therefore, also be useful in the treatment of some forms of cancer.

BRIEF SUMMARY OF THE INVENTION

In one aspect, the present invention provides an isolated and purified cyclic peptide of from 4 to about 13 amino acid residues having (a) an N-terminal amine group, acetyl group (Ac) or a polyethyleneglycol moiety of from about 400 to about 12,000 Daltons average molecular weight ($MPEG_{X000}$) linked through an amide bond to the N-terminal residue; and (b) a C-terminal carboxylic acid group or amide group; the peptide comprising the amino acid residue sequence $Xaa_1$-$Xaa_2$-Asp-$Xaa_3$ (SEQ ID NO:15), where $Xaa_1$ is any L- or D-$\alpha$-amino acid residue and $Xaa_2$ and $Xaa_3$ are any hydrophobic, L-$\alpha$-amino acid residue with the proviso that when $Xaa_1$ is Lys or Arg, $Xaa_2$ cannot be Gly or Cys. In a preferred embodiment, $Xaa_1$ is Phe, Trp or Ile; $Xaa_2$ is Leu, Ile, Val, Lys or Met and $Xaa_3$ is Val, Tyr, Leu, Trp, or Phe. More preferably $Xaa_1$ is Trp and $Xaa_2$ is Leu and $Xaa_3$ is Val.

In one embodiment, a cyclic peptide of the present invention is cyclized via formation of a lactam. Such a peptide comprises the amino acid residue sequence $Xaa_4$-$Xaa_1$-$Xaa_2$-Asp-$Xaa_3$ (SEQ ID NO:1), where $Xaa_1$ is any L- or D-$\alpha$-amino acid residue, $Xaa_2$ is any hydrophobic, L-$\alpha$-amino acid residue with the proviso that when $Xaa_1$ is Lys or Arg, $Xaa_2$ cannot be Gly or Cys; $Xaa_3$ is any hydrophobic, L-$\alpha$-amino acid residue and $Xaa_4$ is any D- or L-$\alpha$-amino acid. Preferably, $Xaa_1$ is Phe or Trp, $Xaa_2$ is Leu, $Xaa_3$ is Val and $Xaa_4$ is Glu. More preferably, such a peptide has the amino acid residue sequence of SEQ ID NO:2–8.

In another embodiment, a cyclic peptide of this invention further comprises a cysteine or modified cysteine residue and a —$CH_2CO$— group at the N-terminal position. In accordance with such an embodiment, $Xaa_1$ is preferably Trp and $Xaa_2$ is preferably Leu. Exemplary and preferred such peptides have the amino acid residue sequence of SEQ ID NO:9–12.

In another embodiment, a cyclic peptide of this invention further comprises two or more cysteine or modified cysteine residues and is cyclized via a disulfide bond. Preferably, one of the cysteine or modified cysteine residues is located at the N- or C-terminal position. In one embodiment, a cyclic peptide having two cysteine or modified cysteine residues comprises the amino acid residue sequence $Xaa_1$-$Xaa_2$-Asp-$Xaa_3$ (SEQ ID NO:15), where $Xaa_1$ and $Xaa_2$ and $Xaa_3$ are as defined above. Preferably, $Xaa_1$ is Tyr, Phe, Trp, dTrp or Ile; $Xaa_2$ is Leu, Ile, Val, Lys, Met or Asp; and $Xaa_3$ is Val, Tyr, Leu, Trp, or Phe.

In yet another embodiment, a cyclic peptide having a cysteine or modified cysteine residue at both the N- and C-terminal positions comprises the amino acid residue sequence of SEQ ID NO:1. Preferably, $Xaa_1$ is Trp or Phe, $Xaa_2$ is Leu, $Xaa_3$ is Val or Tyr and $Xaa_4$ is Ser or Glu.

Exemplary and preferred cyclic, disulfide peptides of the present invention have the amino acid residue sequence of any of SEQ ID NO:13 or 15–43.

In another aspect, the present invention provides a pharmaceutical composition comprising a physiologically acceptable diluent and a cyclic peptide of the present invention. Preferred cyclic peptides in such a composition are the same as set forth above.

In yet another aspect, the present invention provides a process of selectively inhibiting the binding of $\alpha_4\beta_1$ integrin to VCAM-1. That process comprises exposing a cell that expresses $\alpha_4\beta_1$ integrin and a cell that expresses VCAM-1 to an effective inhibiting amount of a cyclic peptide of the present invention. In a preferred embodiment of that process, the VCAM-1 is on the surface of a vascular endothelial cell. In another preferred embodiment, the $\alpha_4\beta_1$ integrin is on the surface of a white blood cell such as a monocyte, a lymphocyte, a granulocyte (an eosinophil or a basophil), a stem cell or other cell that naturally expresses $\alpha_4\beta_1$. Preferred peptides used in that process are the same as set forth above.

Where the cells are located in a living organism, a peptide is preferably administered to the organism in an effective inhibiting amount in a pharmaceutical composition of this invention.

In another aspect, the present invention provides a process of selectively inhibiting the binding of $\alpha_4\beta_1$ integrin to a protein comprising exposing the integrin to the protein in the presence of an effective inhibiting amount of a cyclic peptide of the present invention. Preferably, the $\alpha_4\beta_1$ integrin is expressed on the surface of a cell such as a white blood cell or stem cell and the protein is part of the extracellular matrix such as fibronectin.

DETAILED DESCRIPTION OF THE INVENTION

I. The Invention

The present invention provides a process of inhibiting the binding of $\alpha_4\beta_1$ integrin to proteins such as VCAM-1, fibronectin and invasin. The invention also provides cyclic peptides that inhibit that binding.

The adhesion of leukocytes to the vascular endothelium and their subsequent extravasation into tissues are critical steps in the inflammatory response. Vascular cell adhesion molecule-1 (VCAM-1), a member of the immunoglobulin superfamily, is expressed by endothelial cells and a restricted number of other cell types. VCAM-1 can be induced by cytokines such as tumor necrosis factor-$\alpha_1$, interleukin-4, and interleukin-1$\beta$ and is therefore hypothesized to contribute to leukocyte extravasion in inflammatory conditions such as rheumatoid arthritis, asthma, and atherosclerosis.

One molecular form of VCAM-1 contains seven immunoglobulin modules in its extracellular domain. VCAM-1 is recognized by the integrin receptor $\alpha_4\beta_1$. $\alpha_4\beta_1$ is expressed principally by leukocytes (T and B lymphocytes, monocytes, basophils, and eosinophils), and is also functional on mast cells, derivatives of the embryonic neural crest, and in developing muscle.

$\alpha_4\beta_1$ also recognizes the extracellular matrix glycoprotein fibronectin. Three distinct $\alpha_4\beta_1$-binding sites have been identified within fibronectin and all have been reproduced in synthetic form. One site (represented by the peptide H1) is found in the Hepil region and is therefore expressed in all fibronectin isoforms; two others (represented by peptides CS1 and CS5) are present in the alternatively spliced type III connecting segment. Of these three the CS1 peptide has the higher affinity for $\alpha_4\beta_1$ and contains the tripeptide Leu-Asp-Val (LDV) as its minimal active site. H1 contains a related motif, Ile-Asp-Ala (IDA), while CS5 incorporates a variant of the prototypic RGD motif, Arg-Glu-Asp-Val.

II. Peptides

In one aspect, the present invention provides cyclic peptides that inhibit binding of the $\alpha_4\beta_1$ integrin to VCAM-1. A peptide of the present invention is modeled after the Leu-Asp-Val (LDV) domain of the CS1 peptide sequence, which domain is presented in such a way by the cyclic peptide to produce a potent $\alpha_4\beta_1$ binding inhibitor.

Peptides are disclosed herein as amino acid residue sequences. Those sequences are written left to right in the direction from the amino (N) to the carboxyl (C) terminus. Amino acid residue sequences are denominated by either a single letter or a three letter code. The meanings of those codes as well as various other abbreviations used herein are in accordance with the recommendation of the IUPAC-IUB Joint Commission on Biochemical Nomenclature, and are shown below.

| | | |
|---|---|---|
| A | Ala | L-alanine |
| Ac | | acetyl |
| Aic | | 2-aminoindan-2-carboxylic acid |
| Acm | | acetamidomethyl |
| C | Cys | L-cysteine |
| dC | dCys | D-cysteine |
| C(SO$_3$H) | | L-cysteic acid |
| tBu | | tert-butyl |
| D | Asp | L-aspartic acid |
| dD | dAsp | D-aspartic acid |
| E | Glu | L-glutamic acid |
| dE | dGlu | D-glutamic acid |
| <E | | L-pyroglutamic acid |
| F | Phe | L-phenylalanine |
| G | Gly | glycine |
| H | His | L-histidine |
| I | Ile | L-isoleucine |
| L | Leu | L-leucine |
| K | Lys | L-lysine |
| M | Met | L-methionine |
| N | Asn | L-asparagine |
| P | Pro | L-proline |
| dP | dPro | D-proline |
| dPen | | D-penicillamine |
| Pmc | | 2,2,5,7,8-pentamethylchroman-6-sulphonyl |
| Q | Gln | L-glutamine |
| R | Arg | L-arginine |
| S | Ser | L-serine |
| T | Thr | L-threonine |
| Trt | | trityl |
| V | Val | L-valine |
| W | Trp | L-tryptophan |
| dW | dTrp | D-tryptophan |
| Y | Tyr | L-tyrosine |
| Boc | | tert-butoxycarbonyl |
| DCM | | methylene chloride |
| Dic | | N,N'-diisopropyl carbodiimide |
| DIPEA | | diisopropylethylamine |
| EDT | | 1,2-ethanedithiol |
| Fmoc | | 9-fluorenymethoxy carbonyl |
| HOBT | | 1-hydroxy-1H-benzotriazole |
| HBTU | | O-benzotriazole-N,N,N',N'-tetra-methyluronium-hexafluorophosphate |
| DMF | | N,N-dimethyl formamide |

-continued

| MCPBA | m-chloroperoxy-benzoic acid |
| NMM | N-methylmorpholine |
| TFA | trifluoroacetic acid |

Modifications and changes can be made in the structure of a peptide of the present invention and still obtain a molecule that inhibits the binding of $\alpha_4\beta_1$ integrin to VCAM-1. For example, certain amino acids can be substituted for other amino acids in a sequence without appreciable loss of activity; likewise, D- or L-amino acid residues can be used. D-amino acids are indicated herein as d-Xaa, where Xaa is the three-letter amino acid code (e.g., dTrp). In fact, certain amino acids can be substituted or added which greatly enhance binding inhibition. Because it is the interactive capacity and nature of a peptide that defines that peptide's biological functional activity, certain amino acid sequence substitutions can be made in a peptide sequence and nevertheless obtain a peptide with like properties, particularly inhibition of the binding of $\alpha_4\beta_1$ integrin to VCAM-1. Exemplary such peptides are set forth below.

A peptide contemplated by the present invention is cyclic. A cyclic peptide has a ring structure formed between certain amino acid residues of the corresponding linear peptide and can be envisioned as a linear peptide that is cyclized by covalent bonding of amino acid residues as described herein.

A cyclic peptide of the present invention contains from 4 to about 13 amino acid residues. The N-terminal amino acid residue has a free terminal amine group ($NH_2$), acetyl group (Ac) or a polyethyleneglycol moiety of from about 400 to about 12,000 Daltons average molecular weight ($MPEG_{xooo}$) linked through an amide bond to the N-terminal residue. The C-terminal amino acid residue has a terminal carboxylic acid group (OH) or amide group. A cyclic peptide comprises the amino acid residue sequence $Xaa_1$-$Xaa_2$-Asp-$Xaa_3$ (SEQ ID NO:15), where $Xaa_1$ is any L- or D-α-amino acid residue and $Xaa_2$ and $Xaa_3$ are any hydrophobic, L-α-amino acid residue with the proviso that when $Xaa_1$ is Lys or Arg, $Xaa_2$ cannot be Gly or Cys. In a preferred embodiment, $Xaa_1$ is Phe, Trp or Ile; $Xaa_2$ is Leu, Ile, Val, Lys or Met; and $Xaa_3$ is Val, Tyr, Leu, Trp or Phe. More preferably, $Xaa_1$ is Trp, $Xaa_2$ is Leu and $Xaa_3$ is Val.

A peptide in accordance with the sequence set forth above can be extended in the N-terminal direction by the addition of from 1 to 5 L- or D-α-amino acids and, in the C-terminal direction by the addition of from 1 to 5 L- or D-α-amino acids.

A peptide can be cyclized without or with a sulfur containing bridge. Where a cyclic peptide does not comprise a sulfur containing bridge, the N- and C-terminal amino acid residues are joined together with an amide bond (formally a lactam in the case of cyclization). Where a cyclic peptide comprises a sulfur containing bridge, either one or two amino acid residues of the corresponding linear peptide is a Cys or modified Cys residue (dCys or dPen). Such a cyclic peptide can comprise a cyclic sulfide, sulfoxide or sulfone (one Cys residue in the corresponding linear peptide) or a cyclic disulfide (two Cys residues in the corresponding linear peptide).

Where cyclization has occurred by formation of a lactam by condensation of the N and C terminus, that peptide comprises the amino acid residue sequence:

$Xaa_4$-$Xaa_1$-$Xaa_2$-Asp-$Xaa_3$ (SEQ ID NO:1),
where $Xaa_1$ is any L- or D-α-amino acid residue; $Xaa_2$ and $Xaa_3$ are independently any hydrophobic, L-α-amino acid residue with the proviso that when $Xaa_1$ is Arg or Lys, $Xaa_2$ cannot be Gly or Cys; and $Xaa_4$ is any D- or L-α-amino acid. In a preferred embodiment, $Xaa_1$ is Phe or Trp, $Xaa_2$ is Leu, $Xaa_3$ is Val and $Xaa_4$ is Glu or Ser. Exemplary and preferred peptides in accordance with SEQ ID NO:1 have the sequences Glu-Trp-Leu-Asp-Val-Pro (SEQ ID NO:2), Glu-Trp-Leu-Asp-Val-Asp (SEQ ID NO:3), Glu-Trp-Leu-Asp-Val (SEQ ID NO:4), Glu-Trp-Leu-Asp-Asp (SEQ ID NO:5), Glu-Trp-Leu-Asp-Val-Pro-Glu-Trp-Leu-Asp-Val (SEQ ID NO:6), Gly-Pro-Glu-Phe-Leu-Asp-Val (SEQ ID NO:7) and Glu-Phe-Leu-Asp-Val (SEQ ID NO:8).

Where a peptide of the present invention contains a sulfide, sulfoxide or sulfone bridge, that peptide comprises a cysteine or modified cysteine residue at one position and a —$CH_2CO$— group at the N-terminal position. As used herein, the term "modified cysteine" refers to D-cysteine (dCys) or D-penicillamine (dPen). The sulfur atom of the cysteine or modified cysteine residue is attached to the $CH_2$ group forming the cyclic peptide.

Such a peptide comprises the amino acid residue sequence $Xaa_1$-$Xaa_2$-Asp-$Xaa_3$ (SEQ ID NO:15), where $Xaa_1$, $Xaa_2$ and $Xaa_3$ are as defined above. Preferably, $Xaa_1$ is Trp, $Xaa_2$ is Leu and $Xaa_3$ is Val or Cys. Exemplary and preferred peptides have the sequences $CH_2CO$-Ser-Trp-Leu-Asp-Val-Cys-acid (SEQ ID NO:9), $CH_2CO$-Glu-Trp-Leu-Asp-Val-Cys-acid (SEQ ID NO:10), $CH_2CO$-Glu-trp-Leu-Asp-Cys-acid (SEQ ID NO:11), and $CH_2CO$-Trp-Leu-Asp-Val-Cys-COOH (SEQ ID NO:12).

Where a peptide of the present invention contains a disulfide bridge, that peptide contains two cysteine or modified cysteine residues. Preferably, one of the cysteine or modified cysteine residues is located at the N- or C-terminal position and at least one of those amino acid residues is Cys. Such a disulfide peptide comprises the amino acid residue sequence $Xaa_1$-$Xaa_2$-Asp-$Xaa_3$ (SEQ ID NO:15), where $Xaa_1$, $Xaa_2$ and $Xaa_3$ are as defined above. Preferably, $Xaa_1$ is Trp or Cys, $Xaa_2$ is Leu and $Xaa_3$ is Val or Cys. Exemplary such peptides have the sequence Cys-Leu-Asp-Val-Cys (SEQ ID NO:13) or Cys-Trp-Leu-Asp-Cys-acid (SEQ ID NO:14).

In another preferred embodiment of SEQ ID NO:15, $Xaa_1$ is Tyr, Phe, Trp, dTrp or Ile; $Xaa_2$ is Leu, Ile, Val, Lys, Met or Asp; and $Xaa_3$ is Val, Tyr, Leu, Trp, or Phe. More preferably, a disulfide cyclic peptide has the sequence Cys-Ser-Trp-Leu-Asp-Val-Cys (SEQ ID NO:16), Cys-dTrp-Leu-Asp-Val-Cys-acid (SEQ ID NO:17), Ac-Cys-Trp-Leu-Asp-Val-Cys-acid (SEQ ID NO:18), Cys-Tyr-Leu-Asp-Val-Cys-acid (SEQ ID NO:19), Cys-Trp-Leu-Asp-Phe-Cys-acid (SEQ ID NO:20), Cys-Phe-Leu-Asp-Val-Cys-acid (SEQ ID NO:21), Cys-Trp-Leu-Asp-Trp-Cys-acid (SEQ ID NO:22), Cys-Trp-Ile-Asp-Val-Cys-acid (SEQ ID NO:23), Cys-Trp-Met-Asp-Val-Cys-acid (SEQ ID NO:24), Cys-Trp-Val-Asp-Val-Cys-acid (SEQ ID NO:25), Cys-Trp-Lys-Asp-Val-Cys-acid (SEQ ID NO:26), Cys-Trp-Leu-Glu-Val-Cys-acid (SEQ ID NO:27), Cys-Trp-Leu-Asp-Leu-Cys-acid (SEQ ID NO:28), Cys-Trp-Leu-Asp-Tyr-Cys-acid (SEQ ID NO:29), Cys-Ile-Leu-Asp-Val-Cys-acid (SEQ ID NO:30), Cys-Trp-Leu-Asp-Val-Cys-acid (SEQ ID NO:31), and dCys-Trp-Leu-Asp-Val-Cys-acid (SEQ ID NO:32).

In another preferred embodiment, a disulfide cyclic peptide of the present invention comprises the amino acid residue sequence of SEQ ID NO:1, above. Preferably, $Xaa_1$ is Trp or Phe, $Xaa_2$ is Leu, $Xaa_3$ is Val or Tyr and Xaa4 is Ser or Glu. Exemplary and preferred such peptides have the sequence of Cys-Glu-Trp-Leu-Asp-Val-Cys-amide (SEQ ID NO:33), Cys-Glu-Trp-Leu-Asp-Val-Cys-acid (SEQ ID NO:34), dCys-Glu-Trp-Leu-Asp-Val-Cys-acid (SEQ ID NO:35), Cys-Glu-Trp-Leu-Asp-Tyr-Cys-acid (SEQ ID NO:36), Cys-Ser-Phe-Leu-Asp-Tyr-Cys-acid (SEQ ID NO:37), Cys-Glu-Phe-Leu-Asp-Tyr-Cys-acid (SEQ ID NO:38), dCys-Ser-Trp-Leu-Asp-Val-dCys-acid (SEQ ID NO:39); Cys-Pro-Glu-Trp-Leu-Asp-Val-Cys-acid (SEQ ID NO:40), MPEG$_{5000}$-Cys-Trp-Leu-Asp-Val-Cys-acid (SEQ ID NO:41) and dPen-Trp-Leu-Asp-Val-Cys-acid (SEQ ID NO:42).

In another embodiment, a cyclic disulfide peptide of the present invention comprises the sequence:

Xaa$_n$-Cys-Trp-Leu-Asp-Val-Cys-acid (SEQ ID NO:43), where Xaa is any D- or L-α-amino acid and n is an integer from 1 to 7.

A peptide of the present invention can be made using standard peptide synthetic procedures well known in the art. Typically, peptides were made with Fmoc-amino acids. However, peptides can also be made using Boc protecting groups by methods well known to those skilled in the art. Side chain protecting groups of trifunction amino acids used in the synthetic procedure include Arginine (Pmc), Aspartic acid (tBu), Cysteine (Trt), Glutamic acid (tBu), Histidine (Boc), Lysine (Boc), Serine (tBu), Threonine (tBu), and Tyrosine (tBu). Other protecting groups are specifically described.

The preparation of the peptides in this invention by solid phase methodology is well known to those skilled in the art, and can be described as follows. Peptides were synthesized on an insoluble carrier such as p-benzyloxybenzyl alcohol resin for the synthesis of C-terminal carboxylic acid peptides (Wang resin, where normally the resin can be purchased with the first amino acid bound), and 4-(2',4'-dimethoxyphenyl-Fmoc-aminomethyl)-phenoxy resin for C-terminal amide peptides (Rink resin). The peptides were prepared by solid phase synthesis using either HBTU or DIC chemistry procedures on a Protein Technologies Inc. Symphony peptide synthesizer.

The C-terminal amide peptides were prepared by coupling the C-terminal amino acid of the sequence to the Rink resin using the same general method as the other couplings. The C-terminal carboxylic acid peptides were prepared by purchasing Wang resin to which the C-terminal amino acid was bound to the resin as a carboxylic ester. The α-amino protecting group was removed by piperidine treatment, and the next Fmoc-amino acid coupled to the resin by simultaneous treatment of the resin with the Fmoc-amino acid, a coupling reagent such as DIC or HBTU, and if necessary HOBT. Such deprotection and couplings were repeated to afford each desired peptide. In all cases the Fmoc protecting group was removed by treatment with a 20% solution of piperidine in DMF. However, it is understood by those skilled in the art that the exact percentage of piperidine is not critical and should not be considered limiting in this invention. It is also understood by those skilled in the art that piperidine can be replaced by other bases, furthermore the coupling reagents and protocols used can be substituted with any of those known in the field of peptide synthesis (including the use of Boc chemistry based solid phase synthesis and also solution phase peptide synthesis), and those reagents specifically used in the examples provided should not be considered limiting for this invention. All unnatural amino acids, D-amino acids and other compounds were coupled by manual addition of the reagent, following the same procedure as for automated operation.

Where cyclic sulfides, sulfoxides, sulfones or disulfides with C-terminal carboxylic acids are desired, the peptides can be synthesized on an insoluble carrier such as p-benzyloxybenzyl alcohol resin (Wang resin), whereas the equivalent C-terminal amides were prepared on 4-(2',4'-dimethoxyphenyl-Fmoc-aminomethyl)-phenoxy resin (Rink resin). Where two cysteines are present, mild acid removal of the trityl protecting groups and oxidative cyclization on the resin using DMSO or NIS forms the disulfide bond, and this compound was cleaved from the resin in the normal way. Alternatively disulfides can be prepared by solution phase cyclization of the linear sequence in guanidine hydrochloride. Where cyclic sulfides (and their oxidation products) are desired the N-terminus can be acylated with bromoacetic acid, the cysteine trityl group removed and cyclization achieved by NMM in DMF treatment. The head-tail lactams were synthesized on a chlorotrityl resin which forms a carboxylic ester linkage between the C-terminal amino acid and the resin. The linear peptide was cleaved from the resin with acetic acid in DCM and cyclized in solution to form the lactam.

Peptides were cleaved from the resin with a TFA cocktail after the removal of the N-terminal Fmoc protecting group. The exact composition of the TFA cocktail was varied depending on the side chain protecting groups present, and is well known to those skilled in the art. The range of TFA was from 85 to 95%, and the remainder comprised of a mixture of scavengers selected from a combination of anisole, thioanisole, cresol, thiocresol, phenol, thiophenol, EDT, trimethylsilane and water. The time of the cleavage reaction required is sequence dependant, normally being from 1 to 3 hours. After cleavage, the resin was removed by filtration and cold ether added to the solution to give a precipitate. The precipitate was collected and washed a few times with ether to remove residual TFA and scavengers. The precipitate was redissolved in aqueous solution for lyophilization to give the crude product.

Purification was carried out by reverse-phase HPLC on a $C_{18}$-preparative column (300 Å, 21.4 mm×25 cm, 5 μm spherical packing) at a flow rate of 10 ml/min. The selection of any other suitable packing known to one skilled in the art is equally acceptable. Products were detected by UV absorption at 214 nm. Two mobile phases were used in the HPLC system, solution A and B using a gradient elution. Solution A was comprised of 5% acetonitrile in deionized water containing 0.15% TFA, while solution B was comprised of 5% deionized water in acetonitrile containing 0.1% of TFA. A gradient of increasing percentage of solution B was used to elute the peptide from the solid support, however the gradient used is sequence dependant. Other methods of purification known to one skilled in the art are equally acceptable. The purity of the peptide was checked by $C_{18}$ analytical HPLC (300 Å, 4.6 mm×25 cm, 5 μm spherical packing) at a flow rate of 1 ml/min.

A detailed description of the synthesis of exemplary peptides is set forth hereinafter in the Examples.

II. Pharmaceutical Composition

In another aspect, the present invention provides a pharmaceutical composition comprising a peptide of the present invention and a physiologically tolerable diluent.

The present invention includes one or more peptides as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, or the like.

The compositions can be administered to humans and animals either orally, rectally, parenterally (intravenously, intramuscularly or subcutaneously), intracisternally, intravaginally, intraperitoneally, locally (powders, ointments or drops), or as a buccal or nasal spray or aerosol.

The compositions can also be delivered through a catheter for local delivery at a target site, via an intracoronary stent (a tubular device composed of a fine wire mesh), or via a biodegradable polymer. The compositions may also be complexed to ligands, such as antibodies, for targeted delivery of the compositions.

The compositions are preferably administered by catheter, i.v. or subcutaneous injection, or intranasally via a spray or aerosol.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Besides such inert diluents, the composition can also include adjuvants, such as wetting agents, emulsifying and suspending agents.

Suspensions, in addition to the active compounds, can contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Dosage forms for topical administration of a compound of this invention include ointments, powders, sprays and inhalants. The active component is admixed under sterile conditions with a physiologically acceptable carrier and any preservatives, buffers or propellants as may be required. Ophthalmic formulations, eye ointments, powders and solutions are also contemplated as being within the scope of this invention.

III. Process of Inhibiting the Binding of $\alpha_4\beta_1$

In another aspect, the present invention contemplates a process of selectively inhibiting the binding of $\alpha_4\beta_1$ integrin to VCAM-1. A process of the present invention can be used in vitro or in vivo in a living organism. In accordance with a process of the present invention, a cell expressing $\alpha_4\beta_1$ integrin is exposed to a cell expressing VCAM-1 in the presence of an effective inhibiting amount of a peptide of the present invention. Means for determining an effective inhibiting amount are well known in the art.

A cell expressing $\alpha_4\beta_1$ integrin can be a naturally occurring white blood cell, mast cell or other cell type that naturally expresses $\alpha_4\beta_1$ on the cell surface, or a cell transfected with an expression vector that contains a polynucleotide (e.g., genomic DNA or cDNA) that encodes $\alpha_4\beta_1$ integrin. In an especially preferred embodiment, $\alpha_4\beta_1$ integrin is present on the surface of a white blood cell such as a monocyte, a lymphocyte or a granulocyte (e.g., an eosinophil or a basophil).

A cell that expresses VCAM-1 can be a naturally occurring cell (e.g. an endothelial cell) or a cell transfected with an expression vector containing a polynucleotide that encodes VCAM-1. Methods for producing transfected cells that express VCAM-1 are well known in the art.

Where VCAM-1 exists on the surface of cell, the expression of that VCAM-1 is preferably induced by inflammatory cytokines such as tumor necrosis factor-$\alpha$, interleukin-4 and interleukin-1$\beta$.

Where the cells expressing $\alpha_4\beta_1$ integrin and VCAM-1 are in a living organism, a peptide is administered in an effective amount to the living organism. Preferably, the peptide is in a pharmaceutical composition of this invention. Administering is preferably accomplished via intravascular injection or intranasal administration.

A process of the present invention is especially useful in treating diseases associated with uncontrolled migration of white blood cells to damaged tissue. Such diseases include, but are not limited to, asthma, atherosclerosis, rheumatoid arthritis, allergy, multiple sclerosis, leukemia, and brain cancer.

A process of inhibiting VCAM-1 and $\alpha_4\beta_1$ binding uses a cyclic peptide of the present invention as set forth hereinbefore. Preferred such peptides are the same as set forth above. More preferably, a peptide used in a process of the present invention has the amino acid residue sequence of SEQ ID NO:2–14 or 16–42. Even more preferably, peptides have the amino acid residue sequence of SEQ ID NO:3–7, 9–12, 16–26, 28, 29 or 31–42.

The present invention also provides a process of selectively inhibiting the binding of $\alpha_4\beta_1$ integrin to a protein comprising exposing the integrin to the protein in the presence of an effective inhibiting amount of a cyclic peptide of the present invention. In a preferred embodiment, the $\alpha_4\beta_1$ integrin is expressed on the surface of a cell, either naturally occurring or a cell transformed to express $\alpha_4\beta_1$ integrin.

The protein to which the $\alpha_4\beta_1$ integrin binds can be expressed on a cell surface or part of the extracellular matrix. Especially preferred proteins are fibronectin or invasin. Preferred peptides for use in such a process are the same as set forth above.

The ability of peptides of the present invention to inhibit binding are described in detail hereinafter in the Examples.

The following examples illustrate particular embodiments of the present invention and are not limiting of the specification and claims in any way.

EXAMPLES

Example 1

Synthesis of Cys-TrpLeu-Asp-Val-Cys-acid
(SEQ ID NO:31)

The Fmoc-amino acids and an equimolar amount of HOBT were dissolved in DMF. DIC in DCM was used as the coupling reagent with 1–1.2 hour reaction times. The Fmoc-Cys(Trt) Wang resin (25 nM) was swollen by treatment with DMF (1.5 ml) for 15–20 min, then deprotected by treatment with 20% piperidine in DMF (3×, 8 min each), and the resin was washed with DMF (6×). The first amide bond was formed using Fmoc-Val (150 nM) and DIC (150 nM), and this procedure was repeated until all amino acids were coupled. After deprotection of the N-terminal protecting group, the peptide was cleaved from the resin with a TFA cocktail (containing 5% anisole and 5% EDT) for 1 hour at RT. The TFA solution was reduced to about 0.5 ml and the product precipitated with cold ether. After washing with ether (3×), the peptide was lyophilized from aqueous solution to give the crude linear peptide (21.3 mg). Cyclization was achieved by dissolving in water (20 ml) containing guanidinee. HCl (2.0 g) and ammonium acetate (1.6 g) at pH 7.8, and the solution stirred at 4° C. for 48 hours and then lyophilized.

Purification was carried out by reverse phase HPLC as described above using a gradient of 5–70% B over 60 min, and the pure product isolated as a white powder by lyophilization (10.2 mg, >98% pure by analytical HPLC).

Example 2

Synthesis of dPen-Trp-Leu-Asp-Val-Cys-acid
(SEQ ID NO:42)

This peptide was prepared using the same general procedure as in EXAMPLE 1 for the couplings except using Fmoc-Cys(Acm) Wang resin and Fmoc-Trp(Boc) and Fmoc-dPen(Acm). Cyclization was achieved on the resin by treatment with NIS (4 equiv. for each thiol) in DCM:DMF (2:1) for 3 hours at room temperature. After washing with DMF and DCM the peptide was cleaved with a TFA cocktail and purified by HPLC.

Example 3

Synthesis of CH$_2$CO-Trp-Leu-Asp-Val-Cys-acid
(SEQ ID NO:12)

The linear peptide was prepared as described in EXAMPLE 1, however Fmoc-Trp(Boc) was used in this case. After deprotection of the N-terminal Fmoc group, bromoacetic acid (200 nM), HOBT (200 nM) and DIC (200 nM) in DCM (1.5 ml) was added and the reaction stirred at RT for 1 hour. The Trt group on the Cys residue was removed with 2% TFA in DCM (2.5 ml) which contained 5% of trimethylsilane (4×, 10 min) and then the peptide was cyclized by treatment with 5% NMM in DMF overnight. Oxidation of the sulfide to sulfoxide was achieved with NaIO$_4$ (2.5 equv.) in DMF/DCM/water for 4 hours. The resin was washed with DCM, and the product cleaved and purified as before. Analytical HPLC showed two major peaks corresponding to the two diastereoisomers.

Example 4

Synthesis of CH$_2$CO-Trp-Leu-Asp-Val-Cys-acid
(SEQ ID NO:12)

Synthesis was carried out as in EXAMPLE 3, however oxidation was achieved with MCPBA (6 equiv.) in DCM.

Example 5

Synthesis of -Glu-Trp-MLeu-Asp-Val-Asp-
(SEQ ID NO:3)

This peptide was synthesized on 2-chlorotrityl chloride resin following the same procedure as described in EXAMPLE 1. After removal of the N-terminal Fmoc group the peptide was cleaved from resin using 30% acetic acid in DCM (3×, 10 min). The DCM solution was evaporated, the residue treated with water and lyophilized to give the protected linear peptide. Cyclization was achieved with HBTU (1.2 equv.) in DMF-containing 0.4 M NMM 20–24 hours (1 mg/ml). The DMF was evaporated, and the residue precipitated with water and washed (3×). Deprotection and purification was conducted as described previously.

Example 6

Binding Assays

Peptides were assayed for their ability to inhibit the binding of the integrin $\alpha_4\beta_1$ to VCAM. The specificity of the most potent peptides as inhibitors of $\alpha_4\beta_1$ was determined using a fibronectin binding assay. The assays are described below.

VCAM-1/$\alpha_4\beta_1$ Binding Assay

The assay involves determining the ability of cells that express $\alpha_4\beta_1$ to bind directly to purified VCAM. The integrin-expressing cell type used in this assay was HL-60, a human promyelocytic line.

An expression vector was designed such that a region of VCAM known to bind the integrin was expressed as a fusion protein with mouse IgG. A cDNA containing the two N-terminal domains of human VCAM was generated by the polymerase chain reaction (PCR) from a full length VCAM cDNA. Similarly, a cDNA containing the hinge, CH2 and CH3 regions of mouse IgG$_{2A}$ was amplified by PCR from cDNA made from total RNA isolated from the hybridoma cell line 402C10. The VCAM cDNA was ligated to the mouse IgG cDNA and cloned into a mammalian expression vector. Transfection of the plasmid into COS cells resulted in the expression and secretion of the fusion protein into the surrounding cell culture media.

The media was collected and active protein was purified by immunoprecipitation using Dynal magnetic polystyrene beads coated with goat anti-mouse IgG. Following immunoprecipitation, the beads bound cells that expressed the integrin $\alpha_4\beta_1$ such as Ramos and HL-60. Beads incubated with media from mock transfected COS cells did not bind these cell types and served as a negative control for the assay.

HL-60 cells were fluorescently labeled with Calcein AM C-3099 (Molecular Probes) and resuspended in 1 ml of binding buffer (Hank's balanced salt solution, pH 7.4, 1.0 mM CaCl$_2$, 1.0 mM MgCl$_2$). The beads (10 $\mu$l, 4×10$^6$ beads/ml) were placed in wells of a 96-well microtiter dish with 10 $\mu$l of peptide at various concentrations. The beads were incubated with 10 $\mu$l of labeled cells (10$^7$ cells/ml) for 10 min at room temperature. Following immobilization of the beads onto the plastic with a magnet, unbound cells were removed by washing three times with binding buffer. The remaining bound cells were lysed in 50 mM Tris, pH 7.4, 5.0 mM EDTA, 1.0% NP-40 and quantitated by fluorimetry using a Millipore Cytofluor 2350 fluorimeter. Dose response curves were calculated and IC$_{50}$ values determined. Alternatively, the percent adhesion was determined at a single peptide concentration for comparison among peptides.

Peptides having the amino acid residue sequence of SEQ ID NO:3–7, 9–12, 16–26, 28, 29, and 31–42 were found to significantly inhibit the binding of $\alpha_4\beta_1$ integrin to VCAM-1 at concentrations of peptide less than about 10 $\mu$M.

Fibronectin/$\alpha_4\beta_1$ Binding Assay

The assay accesses the ability of certain peptides to inhibit cells expressing $\alpha_4\beta_1$ but not those expressing $\alpha_4\beta_1$ from binding to fibronectin. The B cell line, Ramos can bind to fibronectin via the $\alpha_4\beta_1$ integrant while binding of the erythroleukemic cell line, K562, is dependent on the integrin $\alpha_4\beta_1$.

Human plasma fibronectin was coated onto wells of a 96 well assay plate. Wells coated with BSA were used as a control for the assay. Following washing with Tris buffered saline, pH 7.4(TBS), the wells were blocked with TBS containing 1% BSA. Ramos and K562 cells that had been fluorescently labelled with Calcein AM C-3099 were washed and resuspended in binding buffer (Hank's balanced salt solution, pH 7.4, 1.0 mM $CaCl_2$, 1.0 mM $MgCl_2$, 1.0 mM $MnCl_2$). Cells were mixed with peptide at various concentrations and placed in the wells. The plate was incubated at 37° C. for 45 min. Following washing, the remaining bound cells were lysed with 1% NP-40 and quantitated by fluorimetry using a Millipore Cytofluor 2350 fluorimeter. Dose response curves were calculated.

The foregoing Examples illustrate particular embodiments of the present invention. One of ordinary skill in the art will readily appreciate that changes, modification and alterations can be made in those embodiments without departing from true scope and spirit of the invention.

What is claimed is:

1. A cyclic disulfide peptide of from 6 to about 8 amino acid residues that inhibits the binding of the integrin $\alpha_4\beta_1$ to VCAM-1 or fibronectin, the peptide having (a) an N-terminal Cys-amine group; and (b) a C-terminal Cys-carboxylic acid or Cys-amide group; said peptide comprising the contiguous amino acid residue sequence $Xaa_1$-$Xaa_2$-Asp-$Xaa_3$ (SEQ ID NO:15), where $Xaa_1$ is Trp, $Xaa_2$ is Leu, and $Xaa_3$ is Val.

2. A cyclic disulfide peptide of from 6 to about 8 amino acid residues that inhibits the binding of the integrin $\alpha_4\beta_1$ to VCAM-1 or fibronectin, the peptide having (a) an N-terminal amine group; and (b) a C-terminal carboxylic acid or amide group; said peptide comprising the contiguous amino acid residue sequence $Xaa_1$-$Xaa_2$-Asp-$Xaa_3$ (SEQ ID NO:15), where $Xaa_1$ is Trp, $Xaa_2$ is Leu, and $Xaa_3$ is Val.

3. The peptide of claim 1 that contains a Glu or a Ser residue between the N-terminal Cys and $Xaa_1$.

4. The peptide of claim 2 that contains a Glu or a Ser residue between the N-terminal Cys and $Xaa_1$.

* * * * *

```
                              SEQUENCE LISTING

<160> NUMBER OF SEQ ID NOS: 43

<210> SEQ ID NO 1
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(2)
<223> OTHER INFORMATION: Xaa is any D- or L-alpha-amino acid
<220> FEATURE:
<221> NAME/KEY: MISC_FEATURE
<222> LOCATION: (3)..(3)
<223> OTHER INFORMATION: Xaa is any hydrophobic L-alpha-amino acid.
<220> FEATURE:
<221> NAME/KEY: MISC_FEATURE
<222> LOCATION: (5)..(5)
<223> OTHER INFORMATION: Xaa is any hydrophobic L-alpha-amino acid.

<400> SEQUENCE: 1

Xaa Xaa Xaa Asp Xaa
1               5

<210> SEQ ID NO 2
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(6)
<223> OTHER INFORMATION: Crosslink between Glu at position 1 and Pro at
      position 6.

<400> SEQUENCE: 2

Glu Trp Leu Asp Val Pro
1               5

<210> SEQ ID NO 3
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(6)
<223> OTHER INFORMATION: Crosslink between Glu at position 1 and Asp at
      position 6

<400> SEQUENCE: 3

Glu Trp Leu Asp Val Asp
```

```
<210> SEQ ID NO 4
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(5)
<223> OTHER INFORMATION: Crosslink between Glu at position 1 and Val at
      position 5.

<400> SEQUENCE: 4

Glu Trp Leu Asp Val
1               5

<210> SEQ ID NO 5
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(5)
<223> OTHER INFORMATION: Crosslink between Glu at position 1 and Asp at
      position 5

<400> SEQUENCE: 5

Glu Trp Leu Asp Asp
1               5

<210> SEQ ID NO 6
<211> LENGTH: 11
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(11)
<223> OTHER INFORMATION: Crosslink between Glu at position 1 and Val at
      position 11

<400> SEQUENCE: 6

Glu Trp Leu Asp Val Pro Glu Trp Leu Asp Val
1               5                   10

<210> SEQ ID NO 7
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(7)
<223> OTHER INFORMATION: Crosslink between Gly at position 1 and Val at
      position 7

<400> SEQUENCE: 7

Gly Pro Glu Phe Leu Asp Val
1               5

<210> SEQ ID NO 8
<211> LENGTH: 5
<212> TYPE: PRT
<213> ORGANISM: Artificial
```

```
<220> FEATURE:
<223> OTHER INFORMATION: Synthetic Sequence
<220> FEATURE:
<221> NAME/KEY: MISC_FEATURE
<222> LOCATION: (1)..(5)
<223> OTHER INFORMATION: Crosslink between Glu at position 1 and Val at
      position 5

<400> SEQUENCE: 8

Glu Phe Leu Asp Val
1               5

<210> SEQ ID NO 9
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Xaa=CH2CH-Ser
<220> FEATURE:
<221> NAME/KEY: MISC_FEATURE
<222> LOCATION: (6)..(6)
<223> OTHER INFORMATION: Xaa=Cys-COOH
<220> FEATURE:
<221> NAME/KEY: MISC_FEATURE
<222> LOCATION: (1)..(6)
<223> OTHER INFORMATION: Crosslink between Xaa at position 1 and Xaa at
      position 6

<400> SEQUENCE: 9

Xaa Trp Leu Asp Val Xaa
1               5

<210> SEQ ID NO 10
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Xaa=CH2CO-Glu
<220> FEATURE:
<221> NAME/KEY: MISC_FEATURE
<222> LOCATION: (6)..(6)
<223> OTHER INFORMATION: Xaa=Cys-COOH
<220> FEATURE:
<221> NAME/KEY: MISC_FEATURE
<222> LOCATION: (1)..(6)
<223> OTHER INFORMATION: Crosslink between Xaa at position 1 and Xaa at
      position 6

<400> SEQUENCE: 10

Xaa Trp Leu Asp Val Xaa
1               5

<210> SEQ ID NO 11
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Xaa=CH2CO-Glu
<220> FEATURE:
<221> NAME/KEY: MISC_FEATURE
<222> LOCATION: (5)..(5)
```

```
<223> OTHER INFORMATION: Xaa=Cys-COOH
<220> FEATURE:
<221> NAME/KEY: MISC_FEATURE
<222> LOCATION: (1)..(5)
<223> OTHER INFORMATION: Crosslink between Xaa at position 1 and Xaa at
      position 5

<400> SEQUENCE: 11

Xaa Trp Leu Asp Xaa
1               5

<210> SEQ ID NO 12
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Xaa=CH2CO-Trp
<220> FEATURE:
<221> NAME/KEY: MISC_FEATURE
<222> LOCATION: (5)..(5)
<223> OTHER INFORMATION: Xaa=Cys-COOH
<220> FEATURE:
<221> NAME/KEY: MISC_FEATURE
<222> LOCATION: (1)..(5)
<223> OTHER INFORMATION: Crosslink between Xaa at position 1 and Xaa at
      position 5

<400> SEQUENCE: 12

Xaa Leu Asp Val Xaa
1               5

<210> SEQ ID NO 13
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(5)
<223> OTHER INFORMATION: Disulfide-bond

<400> SEQUENCE: 13

Cys Leu Asp Val Cys
1               5

<210> SEQ ID NO 14
<211> LENGTH: 5
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (5)..(5)
<223> OTHER INFORMATION: Xaa=Cys-COOH
<220> FEATURE:
<221> NAME/KEY: MISC_FEATURE
<222> LOCATION: (1)..(5)
<223> OTHER INFORMATION: Disulfide-bond

<400> SEQUENCE: 14

Cys Trp Leu Asp Xaa
1               5

<210> SEQ ID NO 15
<211> LENGTH: 4
```

```
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Xaa is any D- or L-alpha-amino acid
<220> FEATURE:
<221> NAME/KEY: MISC_FEATURE
<222> LOCATION: (2)..(2)
<223> OTHER INFORMATION: Xaa is any hydrophobic L-alpha-amino acid
<220> FEATURE:
<221> NAME/KEY: MISC_FEATURE
<222> LOCATION: (4)..(4)
<223> OTHER INFORMATION: Xaa is any hydrophobic L-alpha-amino acid

<400> SEQUENCE: 15

Xaa Xaa Asp Xaa
1

<210> SEQ ID NO 16
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(7)
<223> OTHER INFORMATION: Disulfide-bond

<400> SEQUENCE: 16

Cys Ser Trp Leu Asp Val Cys
1               5

<210> SEQ ID NO 17
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: Xaa=D-Trp
<220> FEATURE:
<221> NAME/KEY: MISC_FEATURE
<222> LOCATION: (6)..(6)
<223> OTHER INFORMATION: Xaa=Cys-COOH
<220> FEATURE:
<221> NAME/KEY: MISC_FEATURE
<222> LOCATION: (1)..(6)
<223> OTHER INFORMATION: Disulfide-bond

<400> SEQUENCE: 17

Cys Xaa Leu Asp Val Xaa
1               5

<210> SEQ ID NO 18
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Xaa=Ac-Cys
<220> FEATURE:
<221> NAME/KEY: MISC_FEATURE
<222> LOCATION: (6)..(6)
<223> OTHER INFORMATION: Xaa=Cys-COOH
```

```
<220> FEATURE:
<221> NAME/KEY: MISC_FEATURE
<222> LOCATION: (1)..(6)
<223> OTHER INFORMATION: Disulfide-bond

<400> SEQUENCE: 18

Cys Trp Leu Asp Val Xaa
1               5

<210> SEQ ID NO 19
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (6)..(6)
<223> OTHER INFORMATION: Xaa=Cys-COOH
<220> FEATURE:
<221> NAME/KEY: MISC_FEATURE
<222> LOCATION: (1)..(6)
<223> OTHER INFORMATION: Disulfide-bond

<400> SEQUENCE: 19

Cys Tyr Leu Asp Val Xaa
1               5

<210> SEQ ID NO 20
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (6)..(6)
<223> OTHER INFORMATION: Xaa=Cys-COOH
<220> FEATURE:
<221> NAME/KEY: MISC_FEATURE
<222> LOCATION: (1)..(6)
<223> OTHER INFORMATION: Disulfide-bond

<400> SEQUENCE: 20

Cys Trp Leu Asp Phe Xaa
1               5

<210> SEQ ID NO 21
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (6)..(6)
<223> OTHER INFORMATION: Xaa=Cys-COOH
<220> FEATURE:
<221> NAME/KEY: MISC_FEATURE
<222> LOCATION: (1)..(6)
<223> OTHER INFORMATION: Disulfide-bond

<400> SEQUENCE: 21

Cys Phe Leu Asp Val Xaa
1               5

<210> SEQ ID NO 22
<211> LENGTH: 6
<212> TYPE: PRT
<213> ORGANISM: Artificial
<220> FEATURE:
```

```
<223> OTHER INFORMATION: Synthetic Sequence
<220> FEATURE:
<221> NAME/KEY: MISC_FEATURE
<222> LOCATION: (6)..(6)
<223> OTHER INFORMATION: Xaa=Cys-COOH
<220> FEATURE:
<221> NAME/KEY: MISC_FEATURE
<222> LOCATION: (1)..(6)
<223> OTHER INFORMATION: Disulfide-bond

<400> SEQUENCE: 22

Cys Trp Leu Asp Trp Xaa
1               5

<210> SEQ ID NO 23
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (6)..(6)
<223> OTHER INFORMATION: Xaa=Cys-COOH
<220> FEATURE:
<221> NAME/KEY: MISC_FEATURE
<222> LOCATION: (1)..(6)
<223> OTHER INFORMATION: Disulfide-bond

<400> SEQUENCE: 23

Cys Trp Ile Asp Val Xaa
1               5

<210> SEQ ID NO 24
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (6)..(6)
<223> OTHER INFORMATION: X=Cys-COOH
<220> FEATURE:
<221> NAME/KEY: MISC_FEATURE
<222> LOCATION: (1)..(6)
<223> OTHER INFORMATION: Disulfide-bond

<400> SEQUENCE: 24

Cys Trp Met Asp Val Xaa
1               5

<210> SEQ ID NO 25
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (6)..(6)
<223> OTHER INFORMATION: Xaa=Cys-COOH
<220> FEATURE:
<221> NAME/KEY: MISC_FEATURE
<222> LOCATION: (1)..(6)
<223> OTHER INFORMATION: Disulfide-bond

<400> SEQUENCE: 25

Cys Trp Val Asp Val Xaa
1               5
```

```
<210> SEQ ID NO 26
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (6)..(6)
<223> OTHER INFORMATION: Xaa=Cys-COOH
<220> FEATURE:
<221> NAME/KEY: MISC_FEATURE
<222> LOCATION: (1)..(6)
<223> OTHER INFORMATION: Disulfide-bond

<400> SEQUENCE: 26

Cys Trp Lys Asp Val Xaa
1               5

<210> SEQ ID NO 27
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (6)..(6)
<223> OTHER INFORMATION: Xaa=Cys-COOH
<220> FEATURE:
<221> NAME/KEY: MISC_FEATURE
<222> LOCATION: (1)..(6)
<223> OTHER INFORMATION: Disulfide-bond

<400> SEQUENCE: 27

Cys Trp Leu Glu Val Xaa
1               5

<210> SEQ ID NO 28
<211> LENGTH: 6
<212> TYPE: PRT
<213> ORGANISM: Artificial
<220> FEATURE:
<223> OTHER INFORMATION: Synthethic Sequence
<220> FEATURE:
<221> NAME/KEY: MISC_FEATURE
<222> LOCATION: (6)..(6)
<223> OTHER INFORMATION: Xaa=Cys-COOH
<220> FEATURE:
<221> NAME/KEY: MISC_FEATURE
<222> LOCATION: (1)..(6)
<223> OTHER INFORMATION: Disulfide-bond

<400> SEQUENCE: 28

Cys Trp Leu Asp Leu Xaa
1               5

<210> SEQ ID NO 29
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (6)..(6)
<223> OTHER INFORMATION: Xaa=Cys-COOH
<220> FEATURE:
<221> NAME/KEY: MISC_FEATURE
<222> LOCATION: (1)..(6)
<223> OTHER INFORMATION: Disulfide-bond

<400> SEQUENCE: 29
```

```
Cys Trp Leu Asp Tyr Xaa
1               5

<210> SEQ ID NO 30
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (6)..(6)
<223> OTHER INFORMATION: Xaa=Cys-COOH
<220> FEATURE:
<221> NAME/KEY: MISC_FEATURE
<222> LOCATION: (1)..(6)
<223> OTHER INFORMATION: Disulfide-bond

<400> SEQUENCE: 30

Cys Ile Leu Asp Val Xaa
1               5

<210> SEQ ID NO 31
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (6)..(6)
<223> OTHER INFORMATION: Xaa=Cys-COOH
<220> FEATURE:
<221> NAME/KEY: MISC_FEATURE
<222> LOCATION: (1)..(6)
<223> OTHER INFORMATION: Disulfide-bond

<400> SEQUENCE: 31

Cys Trp Leu Asp Val Xaa
1               5

<210> SEQ ID NO 32
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Xaa=D-Cys
<220> FEATURE:
<221> NAME/KEY: MISC_FEATURE
<222> LOCATION: (6)..(6)
<223> OTHER INFORMATION: Xaa=Cys-COOH
<220> FEATURE:
<221> NAME/KEY: MISC_FEATURE
<222> LOCATION: (1)..(6)
<223> OTHER INFORMATION: Disulfide-bond

<400> SEQUENCE: 32

Xaa Trp Leu Asp Val Xaa
1               5

<210> SEQ ID NO 33
<211> LENGTH: 7
<212> TYPE: PRT
<213> ORGANISM: Artificial
<220> FEATURE:
<223> OTHER INFORMATION: Synthetic Sequence
<220> FEATURE:
```

```
<221> NAME/KEY: MISC_FEATURE
<222> LOCATION: (7)..(7)
<223> OTHER INFORMATION: Xaa=Cys-NH2
<220> FEATURE:
<221> NAME/KEY: MISC_FEATURE
<222> LOCATION: (1)..(7)
<223> OTHER INFORMATION: Disulfide-bond

<400> SEQUENCE: 33

Cys Glu Trp Leu Asp Val Xaa
1               5

<210> SEQ ID NO 34
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (7)..(7)
<223> OTHER INFORMATION: Xaa=Cys-COOH
<220> FEATURE:
<221> NAME/KEY: MISC_FEATURE
<222> LOCATION: (1)..(7)
<223> OTHER INFORMATION: Disulfide-bond

<400> SEQUENCE: 34

Cys Glu Trp Leu Asp Val Xaa
1               5

<210> SEQ ID NO 35
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Xaa=D-Cys
<220> FEATURE:
<221> NAME/KEY: MISC_FEATURE
<222> LOCATION: (7)..(7)
<223> OTHER INFORMATION: Xaa=Cys-COOH
<220> FEATURE:
<221> NAME/KEY: MISC_FEATURE
<222> LOCATION: (1)..(7)
<223> OTHER INFORMATION: Disulfide-bond

<400> SEQUENCE: 35

Xaa Glu Trp Leu Asp Val Xaa
1               5

<210> SEQ ID NO 36
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (7)..(7)
<223> OTHER INFORMATION: Xaa=Cys-COOH
<220> FEATURE:
<221> NAME/KEY: MISC_FEATURE
<222> LOCATION: (1)..(7)
<223> OTHER INFORMATION: Disulfide-bond

<400> SEQUENCE: 36

Cys Glu Trp Leu Asp Tyr Xaa
1               5
```

<210> SEQ ID NO 37
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (7)..(7)
<223> OTHER INFORMATION: Xaa=Cys-COOH
<220> FEATURE:
<221> NAME/KEY: MISC_FEATURE
<222> LOCATION: (1)..(7)
<223> OTHER INFORMATION: Disulfide-bond

<400> SEQUENCE: 37

Cys Ser Phe Leu Asp Tyr Xaa
1               5

<210> SEQ ID NO 38
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (7)..(7)
<223> OTHER INFORMATION: Xaa=Cys-COOH
<220> FEATURE:
<221> NAME/KEY: MISC_FEATURE
<222> LOCATION: (1)..(7)
<223> OTHER INFORMATION: Disulfide-bond

<400> SEQUENCE: 38

Cys Glu Phe Leu Asp Tyr Xaa
1               5

<210> SEQ ID NO 39
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Xaa=D-Cys
<220> FEATURE:
<221> NAME/KEY: MISC_FEATURE
<222> LOCATION: (7)..(7)
<223> OTHER INFORMATION: Xaa=D-Cys-COOH
<220> FEATURE:
<221> NAME/KEY: MISC_FEATURE
<222> LOCATION: (1)..(7)
<223> OTHER INFORMATION: Disulfide-bond

<400> SEQUENCE: 39

Xaa Ser Trp Leu Asp Val Xaa
1               5

<210> SEQ ID NO 40
<211> LENGTH: 8
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (8)..(8)
<223> OTHER INFORMATION: Xaa=Cys-COOH

```
<220> FEATURE:
<221> NAME/KEY: MISC_FEATURE
<222> LOCATION: (1)..(8)
<223> OTHER INFORMATION: Disulfide-bond

<400> SEQUENCE: 40

Cys Pro Glu Trp Leu Asp Val Xaa
1               5

<210> SEQ ID NO 41
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Xaa is MPEG5000 - Cys, where MPEG is a
      polyethyleneglycol of 5000 molecular weight
<220> FEATURE:
<221> NAME/KEY: MISC_FEATURE
<222> LOCATION: (6)..(6)
<223> OTHER INFORMATION: Xaa=Cys-COOH
<220> FEATURE:
<221> NAME/KEY: MISC_FEATURE
<222> LOCATION: (1)..(6)
<223> OTHER INFORMATION: Disulfide-bond

<400> SEQUENCE: 41

Xaa Trp Leu Asp Val Xaa
1               5

<210> SEQ ID NO 42
<211> LENGTH: 6
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Xaa=D-Pen
<220> FEATURE:
<221> NAME/KEY: MISC_FEATURE
<222> LOCATION: (6)..(6)
<223> OTHER INFORMATION: Xaa=Cys-COOH
<220> FEATURE:
<221> NAME/KEY: MISC_FEATURE
<222> LOCATION: (1)..(6)
<223> OTHER INFORMATION: Disulfide-bond

<400> SEQUENCE: 42

Xaa Trp Leu Asp Val Xaa
1               5

<210> SEQ ID NO 43
<211> LENGTH: 7
<212> TYPE: PRT
<213> ORGANISM: Artificial
<220> FEATURE:
<223> OTHER INFORMATION: Synthetic Sequence
<220> FEATURE:
<221> NAME/KEY: MISC_FEATURE
<222> LOCATION: (1)..(1)
<223> OTHER INFORMATION: Xaa is any D- or L- alpha-amino acid
<220> FEATURE:
<221> NAME/KEY: MISC_FEATURE
<222> LOCATION: (7)..(7)
<223> OTHER INFORMATION: Xaa is Cys-COOH
<220> FEATURE:
<221> NAME/KEY: MISC_FEATURE
<222> LOCATION: (1)..(7)
```

```
<223> OTHER INFORMATION: Disulfide-bond

<400> SEQUENCE: 43

Xaa Cys Trp Leu Asp Val Xaa
1               5
```